United States Patent
Murphy-Chutorian et al.

[11] Patent Number: 6,056,742
[45] Date of Patent: May 2, 2000

[54] REVASCULARIZATION WITH LASER OUTPUTS

[75] Inventors: Douglas R. Murphy-Chutorian, Palo Alto; Richard L. Mueller, Byron; Michael J. Rosinko, San Jose, all of Calif.

[73] Assignee: Eclipse Surgical Technologies, Inc., Sunnyvale, Calif.

[21] Appl. No.: 08/852,011

[22] Filed: May 6, 1997

Related U.S. Application Data

[63] Continuation-in-part of application No. 08/793,000, Feb. 3, 1997.

[51] Int. Cl.[7] ................................................. A61B 17/36
[52] U.S. Cl. ................................................. 606/11; 606/15
[58] Field of Search ........................... 606/7, 10, 11, 606/14–15; 607/24; 600/439

[56] References Cited

U.S. PATENT DOCUMENTS

| | | |
|---|---|---|
| 4,418,688 | 12/1983 | Loeb . |
| 4,448,188 | 5/1984 | Loeb . |
| 4,538,613 | 9/1985 | Rosenberg . |
| 4,641,650 | 2/1987 | Mok . |
| 4,641,912 | 2/1987 | Goldenberg . |
| 4,648,892 | 3/1987 | Kittrell et al. . |
| 4,654,024 | 3/1987 | Crittenden et al. . |
| 4,658,817 | 4/1987 | Hardy . |
| 4,669,467 | 6/1987 | Willett et al. . |
| 4,676,231 | 6/1987 | Hisazumi et al. . |
| 4,682,594 | 7/1987 | Mok . |
| 4,693,556 | 9/1987 | McCaughan, Jr. . |
| 4,706,656 | 11/1987 | Kuboto . |
| 4,718,417 | 1/1988 | Kittrell et al. . |
| 4,719,912 | 1/1988 | Weinberg . |
| 4,745,920 | 5/1988 | Forssman et al. . |
| 4,785,815 | 11/1988 | Cohen . |
| 4,788,975 | 12/1988 | Shturman et al. . |
| 4,827,906 | 5/1989 | Robicsek et al. . |
| 4,850,351 | 7/1989 | Herman et al. . |
| 4,860,743 | 8/1989 | Abela . |
| 4,890,898 | 1/1990 | Bentley et al. . |
| 4,913,142 | 4/1990 | Kittrell et al. . |
| 4,917,084 | 4/1990 | Sinofsky . |
| 4,966,148 | 10/1990 | Millar . |
| 4,967,745 | 11/1990 | Hayes et al. . |
| 4,985,029 | 1/1991 | Hoshino . |
| 4,997,431 | 3/1991 | Isner et al. . |
| 5,093,877 | 3/1992 | Aita et al. . |
| 5,106,386 | 4/1992 | Isner et al. . |
| 5,125,926 | 6/1992 | Rudko et al. . |
| 5,203,779 | 4/1993 | Müller et al. .............................. 606/15 |
| 5,380,316 | 1/1995 | Aita et al. . |
| 5,389,096 | 2/1995 | Aita et al. . |
| 5,431,628 | 7/1995 | Millar . |
| 5,503,156 | 4/1996 | Millar . |
| 5,554,152 | 9/1996 | Aita et al. . |
| 5,672,170 | 9/1997 | Cho et al. . |
| 5,674,217 | 10/1997 | Wahlstrom et al. ....................... 606/15 |
| 5,693,043 | 12/1997 | Kittrell et al. ............................. 606/15 |

FOREIGN PATENT DOCUMENTS 29610320  6/1996  Germany .

OTHER PUBLICATIONS

Rissel, U. et al., "A New 2–Channel Stimulation Device with Integrated Ablation–control Unit for the Diagnosis and Treatment of Cardiac Arrythmias," Biomed. Technik 33 (1988) pp. 18–25.

(List continued on next page.)

*Primary Examiner*—Francis J. Jaworski
*Attorney, Agent, or Firm*—Wilson Sonsini Goodrich & Rosati

[57] ABSTRACT

Apparatus for treating a patient's heart by stimulating revascularization of the heart or creating channels in the heart. The apparatus includes a catheter, a laser energy source coupled to the catheter, and a control circuit. The control circuit is configured to cause the laser energy source to deliver an output of laser energy over a first time period shorter than a heart beat cycle.

35 Claims, 11 Drawing Sheets

OTHER PUBLICATIONS

English Translation of Biomed. Technik Article.

Abela et al., Effects of Carbon Dioxide, Nd–YAG, and Argon Laser Radiation on Coronary Atheromatous Plaques, The American Journal of Cardiology, vol. 50, Dec. 1982, pp. 1199–1205.

Abela et al., Laser Recanalization of Occluded Atherosclerotic Arteries In Vivo and In Vitro, Laboratory Investigation, Coronary Artery Disease, vol. 71, No. 2, Feb. 1985, pp. 403–411.

Anderson et al., Coaxial Laser Energy Delivery Using a Steerable Catheter in Canine Coronary Arteries, American Heart Journal, Jan. 1987, pp. 37–48.

H.T. Aretz et al., Intraluminal Ultrasound Guidance of Transverse Laser Coronary Atherectomy, SPIE vol. 1201 Optical Fibers in Medicine V (1990), pp. 68–78.

Bogen et al., Is Catheter Ablation on Target, The American Journal of Cardiology, vol. 60, Dec. 1, 1987, pp. 1387–1392.

Bommer et al., Laser Atrial Septostomy, American Heart Journal, Nov. 1983, pp. 1152–1156.

Bowker et al., Laser Assisted Coronary Angioplasty, European Heart Journal, © 1988, pp.25–29.

Choy et al., Laser Coronary Angioplasty: Experience with 9 Cadaver Hearts, The American Journal of Cardiology, vol. 50, Dec. 1982, pp. 1209–1211.

Choy et al., Transluminal Laser Catheter Angioplasty, The American Journal of Cardiology, vol. 50, Dec. 1982, pp. 1206–1208.

Cox et al., Laser Photoablation for the Treatment of Refractory Ventricular Tachycardia and Endocardial Fibroelastosis, The Annals of Thoracic Surgery, vol. 39, No. 3, Mar. 1985, pp. 199–200.

Davi et al., Continuous Wave (CW) and Pulsed Laser Effects on Vascular Tissues and Occlusive Disease in Vitro, Lasers in Surgery and Medicine 5:239—250 © 1985 Alan R. Liss, Inc.

Desilets et al., A New Method of Percutaneous Catheterization, Radiology, 85, Jul. 1965, pp. 147–148.

Goda et al., Myocardial Revascularization by CO2 Laser, © 1987 S. Karger AG Basel, Eur. surg. Res. 19; pp. 113–117.

Grundfest et al., Laser Ablation of Human Atherosclerotic Plaque Without Adjacent Tissue Injury, Laser Angioplasty: Morphologic Studies, JACC, Apr. 1985, pp. 929–933.

Hardy et al., Regional Myocardial Blood Flow and Cardiac Mechanics in Dog Hearts with CO2 Laser–induced Intramyocardial Revascularization, Basic Research in Cardiology, vol. 85, No. 2, 1990, pp. 179–197.

Isner et al., Identification of Photoproducts Liberated by In Vitro Argon Laser Irradiation of Atherosclerotic Plaque, Calcified Cardiac Valves and Myocardium, The American Journal of Cardiology, Apr. 1985, pp. 1192–1196.

Isner et al., Laser–Assisted Debridement of Aortic Valve Calcium, Amer. Heart Journal, Mar. 1985, pp. 448–452.

Isner et al., Laser–Assisted Endocardiectomy for Refractory Ventrical Tachyarrhythmias: Preliminary Intraoperative Experience, Clinical Cardiology, vol. 10, Mar. 1987, pp. 201–204.

Isner, et al., Laser Myoplasty for Hypertrophic Cardiomyopathy, Jun. 1, 1984, The American Journal of Cardiology, vol. 53, pp. 1620–1625.

Isner et al., Laser Photoablation of Pathological Endocardium: In Vitro Findings Suggesting a New Approach to the Surgical Treatment of Refractory Arrhythmias and Restrictive Cardiomyopathy, The Annals of Thoracic Surgery, vol. 39, No. 3, Mar. 1985, pp. 201–206.

Jeevanandam et al., Myocardial Revascularization by Laser– Induced Channels, Surgical Forum XLI, Oct. 1990, pp. 225–227.

Josephson et al., Endocardial Excision: A New Surgical Technique for the Treatment of Recurrent Ventricular Tachycardia, Circulation, vol. 60, No. 7, Dec. 1979, pp. 1430–1439.

Kjellstrom et al., The Use of Lasers in Vascular and Cardiac Surgery, Acta Chir Scand 153, 1987, pp. 493–499.

Lee et al., Effects of Laser Irradiation Delivered by Flexible Fiberoptic System on the Left Ventricular Internal Myocardium, Sep., 1983, American Heart Journal, pp. 587–590.

Lee et al., Laser–Dissolution of Coronary Atherosclerotic Obstruction, American Heart Journal, Dec. 1981, pp. 1074–1075.

Lee et al., Potential Complications of Coronary Laser Angioplasty, American Heart Journal, Dec. 1984, pp. 1577–1579.

Lee et al., Transcatheter Ablation: Comparison between Laser Photoablation and Electrode Shock Ablation in the Dog, Mar. 1985, Laboratory Investigation, Laser Photoablation, vol. 71, pp. 579–586.

Masayoshi et al., Current Problems in Coronary Artery Surgery: New Methods for Myocardial Revascularization and Vascular Anastomosis, Jan., 1960, pp. 1203–1207.

Mirhoseini et al., Clinical and Histological Evaluation of Laser Myocardial Revascularization, Journal of Clinical Laser Medicine & Surgery, Jun. 1990, pp. 73–78.

Mirhoseini et al., Clinical Report: Laser Myocardial Revascularization, © Alan R. Liss, Inc., Lasers in Surgery and Medicine 6:459–461 (1986).

Mirhoseini, Laser Applications in Thoracic and Cardiovascular Surgery, Medical Instrumentation, vol. 17, No. 6, 11–12, 1983, © 1983 Association for the Advancement of Medical Instrumentation.

Mirhoseini, Laser Revascularization of the Heart, New Frontiers in Laser Medicine and Surgery, ISBN Elsevier Science Publishing Co., pp. 296–303.

Mirhoseini et al., Lasers in Cardiothoracic Surgery, Chapter 21, pp. 216–232.

Mirhoseini et al., Myocardial Revascularization by Laser: A Clinical Report, © 1983 Alan R. Liss, Inc., Lasers in Surgery and Medicine 3:241–245.

Mirhoseini et al., New Concepts in Revascularization of the Myocardium, The Annals of Thoracic Surgery, vol. 45, No. 4, Apr. 1988, pp. 415–420.

Mirhoseini et al., Revascularization of the Heart by Laser, Journal of Microsurgery, Jun. 1981, pp. 253–260.

Mirhoseini, Transventricular Revascularization by Laser, Lasers in Surgery and Medicine, 2:187–198(1982).

Okada et al., Alternative Method of Myocardial Revascularization by Laser: Experimental and Clinical Study, Kobe J. Medical Science 32, Oct. 1986, pp. 151–161.

Regna, Abstract of U.S. application No. 4,796,630; Filed: Jan. 10, 1989.

Riemenschneider et al., Laser Irradiation of Congenital Heart Disease: Potential for Palliation and Correction of Intracardiac and Intravascular Defects, American Heart Journal, Dec. 1983, pp. 1389–1393.

Saksena et al., Laser Ablation of Normal and Diseased Human Ventricle, Jul. 1986, American Heart Journal, pp. 52–60.

Selle et al., Successful Clinical Laser Ablation of Ventricular Tachycardia: A Promising New Therapeutic Method, Ann Thorac Surg, Oct. 1986, pp. 380–384.

Svenson et al., Neodymium: YAG Laser Photocoagulation: A Succussful New Map–Guided Technique for the Intraoperative Ablation of Ventricular Tachycardia, Therapy and Prevention—Laser Photocoagulation, vol. 76, No. 6, Dec. 1987, pp. 1319–1328.

van Gemert et al., Optical Properties of Human Blood Vessel Wall and Plaque, Lasers in Surgery and Medicine, vol. 5, 1985, pp. 235–237.

White, Angioscopy and Lasers in Cardiovascular Surgery: Current Applications and Future Prospects, Aust. N.Z.. Surg. 1988, pp. 271–274.

Zeevi et al., The Use of Carbon Dioxide Fiberoptic Laser Catheter for Atrial Septostomy, American Heart Journal, Jul. 1988, pp. 117–122.

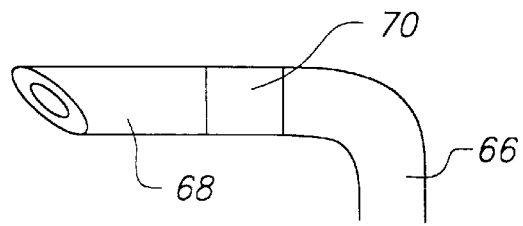
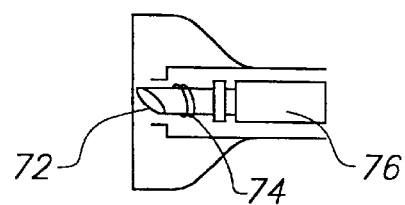
FIG. 4c    FIG. 4d
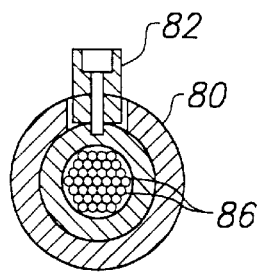
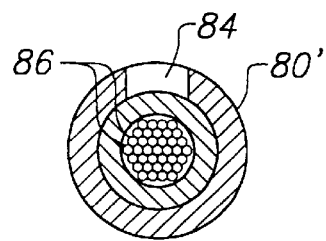
FIG. 5a    FIG. 5b
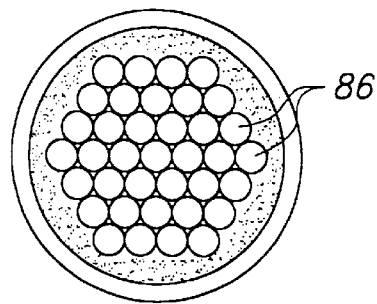
FIG. 5c
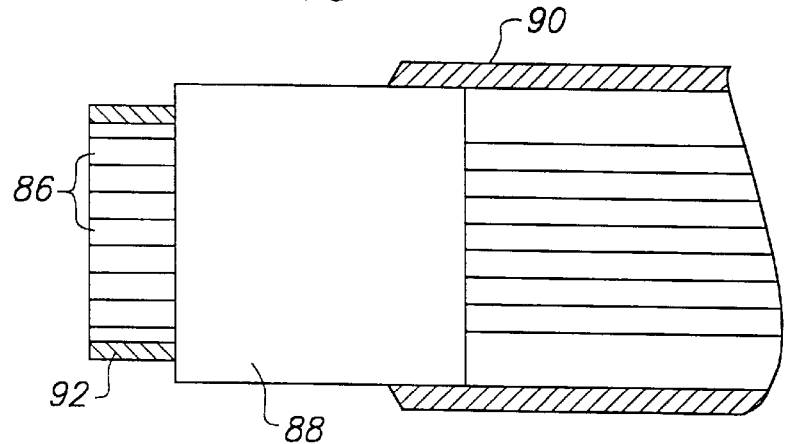
FIG. 5d

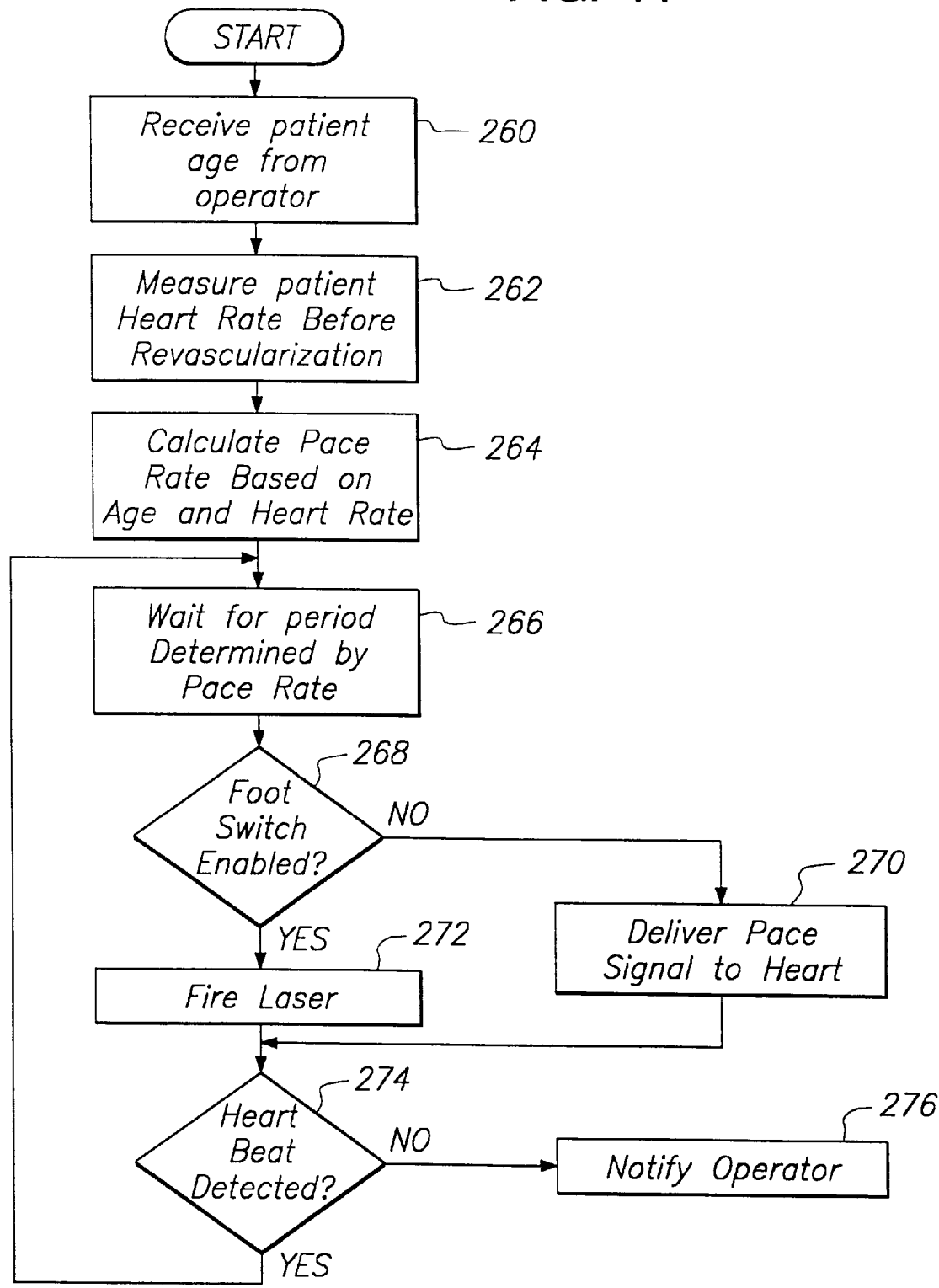

REVASCULARIZATION WITH LASER OUTPUTS

CROSS-REFERENCE TO RELATED APPLICATIONS

This application is a continuation in part application of U.S. patent application entitled REVASCULARIZATION WITH HEART PACING, application Ser. No. 08/793,000, Filed on Feb. 3, 1997, inventors: Murphy-Chutorian, Mueller.

The following applications are hereby incorporated herein by reference: U.S. patent application Ser. No. 08/852,977 Entitled ULTRASOUND DEVICE FOR AXIAL RANGING, Inventor(s): Zanelli, et. al. U.S. patent application Entitled METHOD AND APPARATUS FOR CREATION OF DRUG DELIVERY AND/OR STIMULATION POCKETS IN THE MYOCARDIUM, application Ser. No. 08/773,778, Filed on Dec. 23, 1996, inventor(s): Mueller; U.S. patent application Entitled METHOD AND APPARATUS FOR MECHANICAL TRANSMYOCARDIAL REVASCULARIZATION OF THE HEART, U.S. Pat. No. 5,871,495, Filed on Sep. 13, 1996, inventor(s): Mueller; U.S. patent application Entitled METHOD FOR NON-SYNCHRONOUS LASER ASSISTED TRANSMYOCARDIAL REVASCULARIZATION, U.S. Pat. No. 5,785,702, filed on Oct. 15, 1996, inventor(s): Murphy-Chutorian; and U.S. Patent Application Entitled MINIMALLY INVASIVE METHOD FOR FORMING REVASCULARIZATION CHANNELS, Application No. 08/794,733, inventor(s) Daniel et. al.

BACKGROUND OF THE INVENTION

1. Field of the Invention

This invention relates generally to a method and apparatus for revascularization of a heart, and more particularly to a method and apparatus for revascularization using laser outputs.

2. Description of Related Art

Heart disease is a significant health problem which has been the subject of substantial medical study. By-pass surgery has become commonplace, yet such surgery may only partially correct a diminished blood supply to heart muscle and may be unavailable to many patients, either because of the nature of the occlusions or the physical condition of the patient.

One promising alternative or adjunctive technique for treating such cases is known as transmyocardial revascularization (TMR). This technique was considered in the work of Dr. C. Beck in "the Development of a New Blood Supply to the Heart by Operation," *Annals of Surgery Annals of Surgery*, Vol. 102, No. 5 (11/35) pp. 801–813. The method was also studied in the work of Dr. M. Mirhoseini and M. Cayton, an example of which is found in "Lasers and Cardiothoracic Surgery" in Lasers in General Surgery (Williams and Williams, 1989) pp. 216–223. A device to perform TMR is described in Aita et al., U.S. Pat. No. 5,380,316, issued Jan. 10, 1995. In TMR generally the surgeon creates narrow channels in the heart at the surface of a ventricle of the heart. The surgeon generally uses a laser to create these channels either by accessing the endocardium through a percutaneous route or the epicardium through an incision in the chest wall. The pressure within the left ventricle during systole forces oxygenated blood into the channels and consequently oxygenates the ischemic myocardium of the left ventricle.

It is desirable to be able to control the time point within the cycle of heartbeats at which the heart is revascularized. A heart synchronized pulse laser system which operates on a beating heart between the R and T waves of the electrocardiogram (ECG) signal is described in U.S. Pat. No. 5,125,926 (Rudko).

An electrocardiogram signal may not always provide the most accurate indication of heart function. Further, the electrocardiogram signal is a passive indication of heart rate. It is not a method to control the rate at which the heart beats.

There is a need for an apparatus for stimulating revascularization of the heart or creating channels in the heart where the revascularization event caused by the revascularization device can occur at a selected time in relation to the heartbeat. There is a further need for an apparatus for treating a heart by stimulating revascularization of the heart or creating channels in the heart where the device can control the heartbeat rate. There is further need to reduce the number of cycles over which a laser must be fired to achieve the desired depth of channels in the heart.

SUMMARY OF THE INVENTION

Accordingly, an object of the invention is to provide an apparatus for stimulating revascularization of the beating heart or creating channels in the heart.

Further, an object of the invention is to provide an apparatus for stimulating revascularization of the heart or creating channels in the heart where the revascularization or creation of channels occurs at a time when the heart is less sensitive to external influences.

Another object of the invention is to provide an apparatus for stimulating revascularization of the heart or creating channels in the beating heart where the revascularization or creation of channels occurs when the beating heart is relatively still.

A further object is to reduce the number of cycles over which the laser must be fired.

Another object of the invention is to provide an apparatus for stimulating revascularization of the heart or creating channels in the heart where the revascularization event caused by the revascularization device can occur at a selected time in relation to the heartbeat.

Another object of the invention is to provide an apparatus for treating a heart by stimulating revascularization of the heart or creating channels in the heart where the device can control the heartbeat rate.

These and other objects are achieved in an apparatus for treating a patient's heart by stimulating revascularization of the heart or creating channels in the heart. In one embodiment the apparatus includes a catheter, a laser energy source coupled to the catheter, and a control circuit. The control circuit is configured to cause the laser energy source to deliver an output of laser energy over a first time period shorter than a heart beat cycle.

In one embodiment, the set of laser pulses comprises a number of laser pulses sufficient to cause one heartbeat per set of laser pulses. In one embodiment the set of laser pulses comprises a number of laser pulses to cause no more than one heartbeat per set of laser pulses.

Embodiments of the invention include methods of revascularization and a computer program product for revascularization.

BRIEF DESCRIPTION OF THE FIGURES

FIG. 4c is a perspective view of a piercer with an electrode.

FIG. 4d is a cross sectional view of an electrically controllable mechanical cutter.

FIG. 5a is a cross sectional view of a catheter with fiber optic fibers.

FIG. 5b is a cross sectional view of a catheter with fiber optic fibers.

FIG. 5c is a cross sectional view of a catheter with fiber optic fibers.

FIG. 5d is a cross sectional view of a catheter with fiber optic fibers.

FIG. 14 is a flow chart showing a program for revascularization with sensor verify and pace rate calculation.

DETAILED DESCRIPTION

Figure 1:
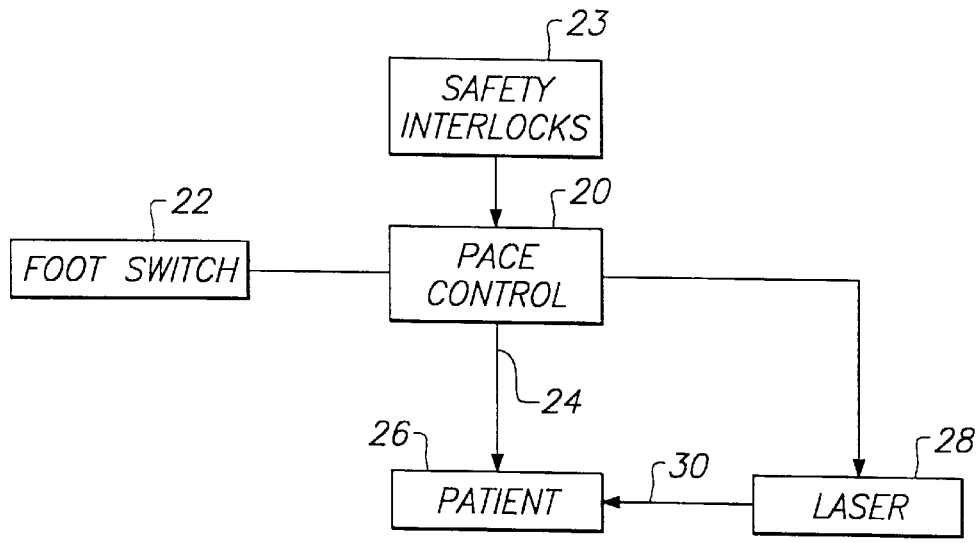
FIG. 1 is a block diagram of a system for performing transmyocardial revascularization.

The apparatus and method of the present invention create channels or stimulation zones or both in the heart through a series of revascularization events. A revascularization device is used to create channels or stimulation zones in the heart. A revascularization device is one or more laser energy delivery devices (fired alone, simultaneously, or sequentially), a mechanical cutter, an ultrasound energy delivery device, or other device or devices for creating channels in heart tissue. A revascularization event is an action of the revascularization device as the device cuts, burns, lases, or otherwise creates or lengthens channels in the heart tissue. The channels or stimulation zones allow for improved bloodflow in heart tissue and/or help to stimulate regrowth of capillaries.

In an embodiment of the invention, revascularization energy is delivered to the heart in the form of an output of laser energy. An output of laser energy may include multiple laser pulses delivered during a time period generally not greater than a heart beat cycle. An output may also include a continuous wave of laser energy. The burst may create a single heart beat.

In another embodiment of the invention, heart function is sensed after energy is delivered to the heart to cause the heart to beat. If a heartbeat is not detected, then the operator is notified. If a heartbeat is detected, a revascularization event is delivered to the heart.

Embodiments of the present invention provide revascularization events to the heart at a specific time in the heartbeat cycle. In some embodiments of the invention the heart is paced. A pace signal starts a heartbeat cycle. A revascularization event is provided to the heart relative to the pace signal. By timing the revascularization event with respect to the pace signal, the revascularization event is provided at a selected time within the created heartbeat cycle.

The time within the cycle between the two created heartbeats at which the revascularization event occurs can be selected to provide an optimal time at which to cause a revascularization event to occur. The time delay can be selected so that the revascularization occurs when the heart is less sensitive to external stimuli, or when the heart is more quiet so as to reduce the risk to the patient and help achieve better revascularization. After the created heartbeat is created, a revascularization period begins and during the revascularization period a revascularization event is caused to occur.

An energy source, including but not limited to a pacemaker, is used to pace the heart and cause the heart to beat at a selected rate. The surgeon may enable the revascularization apparatus with a foot switch. A control circuit receives input from the surgeon's foot switch. The control circuit causes the revascularization device to start a revascularization event at a time relative to the time the energy source causes the heart to beat. Among the advantages of pacing the heart while performing revascularization is that the surgeon can control the rate of the heart and not have to rely exclusively on the natural rhythms of a possibly compromised or sick heart.

Referring now to FIG. 1, the surgeon enables the apparatus through footswitch 22. Pace control block 20 receives a signal from safety interlocks 23 and footswitch 22, which is operated by the surgeon. Pace control block 20 outputs signals to pacing leads 24 which provide a pacing signal to patient 26. The pacing signal causes a created heartbeat and causes the patient's heart to beat at the pace rate provided by pace control block 20. Pace control block 20 sends a signal to a laser 28 to cause laser 28 to provide laser energy through optical fiber 30 to the patient's heart at a selected time in relation to the created heartbeat. The energy provided through optical fiber 30 is used to revascularize or to create channels in the heart of patient 26.

Figure 2:
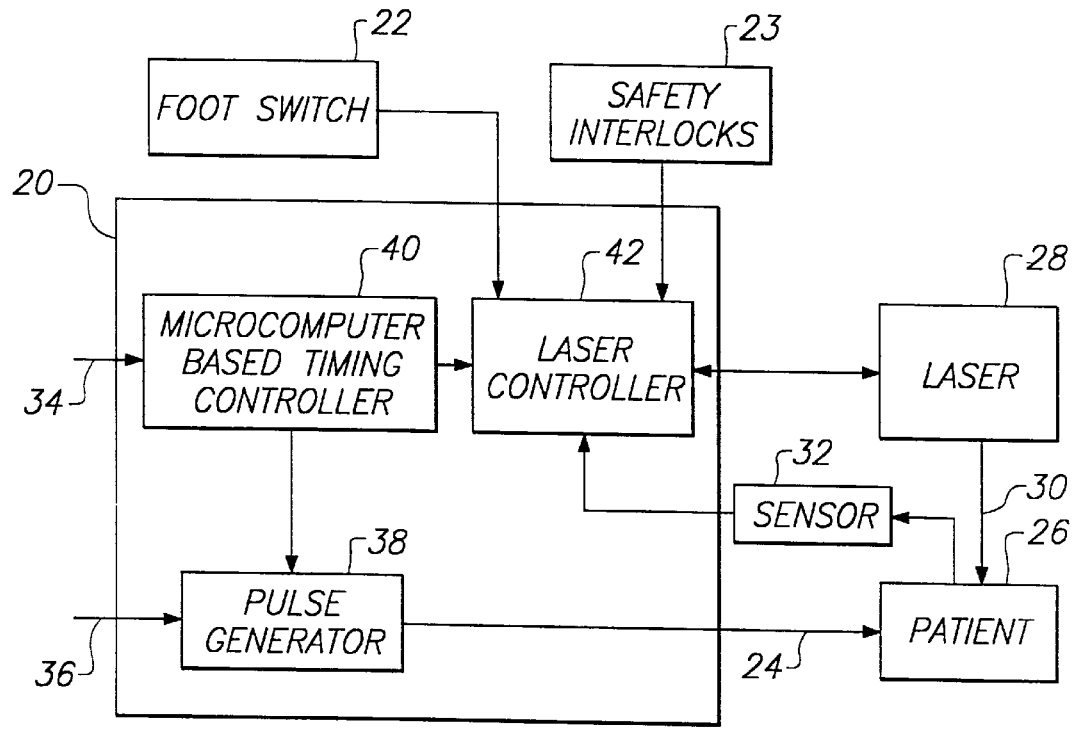
FIG. 2 is a block diagram of a system for performing transmyocardial revascularization including a block diagram of a pulse generator.

Referring now to FIG. 2, pace control block 20 includes microcomputer based timing controller 40, pulse generator 38, and laser controller 42. Desired rate 34 is coupled to a microcomputer based timing controller 40 and controls the rate at which pulse generator 38 provides pacing signals to patient 26 via pacing leads 24. Desired current 36 is coupled to pulse generator 38 and controls the level of current that is provided to patient via pacing leads 24 in order to pace the patient's heart. The output of microcomputer based timing controller 40 provides timing signals to laser controller 42. The timing signals cause the revascularization event to occur at the selected time relative to the created heartbeat created by pulse generator 38. The input of sensor 32 is coupled to patient 26. Sensor 32 is not necessary for the operation of the system and is therefore optional. The optional signal from sensor 32 is a heartbeat indicator signal. The heartbeat indicator signal indicates whether the patient's heart is beating. The output of footswitch 22, safety interlocks 23, timing signals from microcomputer based timing controller 40, and the output of sensor 32 are combined in laser controller 42 to provide a laser active signal to laser 28. Thus, a signal is provided only when all of the following occur: the surgeon has enabled the system via the footswitch, the safety interlocks are enabled, the optional heartbeat indicator indicates that the heart is beating, and a signal is provided to fire the laser from the output of microcomputer based timing controller 40. Laser 28 provides laser energy over optical fiber 30 in order to create a revascularization event in the heart to stimulate revascularization of the heart of patient 26 or to create channels in the heart to improve blood flow.

In an alternative embodiment signals from foot switch 22 or from sensor 32 or both could be input into microcomputer based timing controller 40 instead of into laser controller 42. In such a configuration, microcomputer based timing controller 40 would then provide appropriate signals to laser controller 42 partially in response to signals from foot switch 22 or from sensor 32. Also, instead of providing control to pulse generator 38, microcomputer based timing controller 40 could receive information from pulse generator 38 regarding the timing of pulses and then microcomputer based timing controller 40 would provide control to laser controller 42 in response to the timing of pulses. Microcomputer based timing controller 40 is a microcomputer that runs a set of software instructions recorded in a memory. Alternatively, integrated circuit logic may be used to perform the function of microcomputer based timing controller 40.

Pulse generator 38 provides the pacing signal to the patient's heart or to another location on the patients body in order to pace the patient's heart via pacing leads 24. Pulse generator 38 may be a heart pacemaker such a modified model 540 External Pulse Generator, SeaMED Corp., Redmond, Wash. The pacemaker is modified such that it generates a pulse to the pacing leads when it receives an external logic signal. Alternatively, pulse generator 38 is any artificial energy source capable of causing the heart to beat. For example, the same revascularization device used to create channels, such as a laser, may be used to pace the heart as channels are created by timing the revascularization events to match the natural heart rate or to synchronize with the heart rate. In such a case where a laser or other revascularization device is used to pace the heart, the artificial energy source and the revascularization are the same device.

The pace rate is determined by desired rate 34 and can be set by the operator. The rate of pace unit 38 is optimally set to a rate faster than the normal heartbeat rate. Heartbeat rate can be determined manually or by sensor 32 or by any other method or heartbeat rate measurement. If the signal from sensor 32 is provided to microcomputer based timing controller 40, then controller 40 optionally uses the output information from the sensor 32 to determine the patient's heart rate before the patient's heart is paced and optionally calculates and applies a pace rate faster than the unpaced heartbeat rate. If microcomputer based timing controller 40 is configured to automatically deliver a pace rate faster than the unpaced heartbeat rate, the automatically determined pace rate can be manually overridden by the operator. Sensor 32 can be an electrocardiogram unit, a pressure transducer, a Doppler effect heartbeat rate sensor, or other sensor to measure heart function.

In a preferred embodiment laser 28 is a holmium laser available as an Eclipse 40001 holmium laser from Eclipse Surgical Technologies, Inc., Sunnyvale, Calif. Other types of medical lasers may also be used, for example, an excimer laser, a CO. laser, an Argon laser, a Nd-yag laser, an erbium laser, or a diode laser. A medical laser having a wavelength in the range of 308 milimeters to 10.6 micrometers may be used. A single laser may be used, or multiple lasers or multiple fibers from a single laser can be used in order to cause more revascularization to occur at one time. For a discussion of tuning of a laser for revascularization, see U.S. Patent Application entitled Method for Non-Synchronous Laser Assisted Transmyocardial Revascularization, Application No. 08/729325, filed on Oct. 15, 1996, which is incorporated herein by reference. As an alternative to a laser revascularization device, another revascularization device such as a mechanical cutter or an ultrasound energy delivery device may be used in order to create channels in the heart or to revascularize the heart. The revascularization device can be coupled to a catheter for percutaneous and minimally invasive surgery (MIS) approaches. Alternatively, the revascularization device can be used directly in open heart surgery. If the revascularization device is coupled to a catheter, it can be introduced percutaneously and moved into the heart through the vasculature.

Microcomputer based timing controller 40 can be configured so that the time delay from the pace signal created by the pulse generator 38 to the time of the revascularization event is a fixed time. A 120 ms delay is generated as a default. Alternatively, the microcomputer based timing controller 40 can be configured so that the time delay from the signal from the pulse generator 38 to the revascularization event is a variable time. The revascularization time may be variable so that it is shorter when revascularization is taking place closer to the sinus node and longer when revascularization is taking place further away. The varying delay may be controlled as set by the operator or automatically varied. The time delay can be set to cause the revascularization event to occur at a chosen point within the created heartbeat cycle. This chosen point in time can be chosen so as to cause the least amount of interference or irritation to the heart. The point in time may be chosen to be the point at which the heart is relatively quiet electrically. This point may also be chosen to be the point at which the heart is mechanically still. In particular, the revascularization event may be caused to occur after a depolarization of the heart and before a repolarization of the heart. The revascularization event may be caused to occur after an R wave and before a T wave produced by the heart. Microprocessor based timing controller 40 can be configured to have a fixed or variable number of pulses, and variable or fixed pulse repetitive interval. Microcomputer based timing controller 40 controls the frequency and duration of laser outputs and the resulting revascularization events and thus has an effect on the amount of revascularization or on the depth of the channel created in the heart during the revascularization event.

In an alternative embodiment, microcomputer based timing controller 40 is configured to cause laser 28 to deliver multiple laser pulses for each pace signal which are used to help create a greater depth of revascularization per heartbeat or to create a series of stimulation pockets connected by narrow channels. If multiple lasers or multiple fibers from one laser are used, then multiple channels can also be created simultaneously. In another embodiment, microcomputer based timing controller 40 can be configured to cause laser 28 to deliver revascularization events to the patient's heart at a time in the heartbeat cycle so that the revascularization event also causes a heartbeat. After a beat is created by a laser pulse, another laser pulse is delivered to create a revascularization event. In this mode of operation when footswitch 22 is activated, the pulse generator 38 is disabled and one or more revascularization events are delivered to patient's 26 heart during a time that the pacemaker signal would have been delivered. In this manner the laser can be used to pace the patients heart.

Optical fiber 30 may be introduced into patient 26 via a catheter in a percutaneous procedure. Alternatively, optical fiber 30 can be provided to patient 26 through open heart surgery or MIS techniques. A laser energy delivery device provides the energy from the laser 28 to the heart of patient 26. In FIG. 2 the laser energy delivery device is shown as an optical fiber. Other forms of laser energy delivery devices could also be used to provide energy from a laser to the heart of patient 26.

Figure 3A:
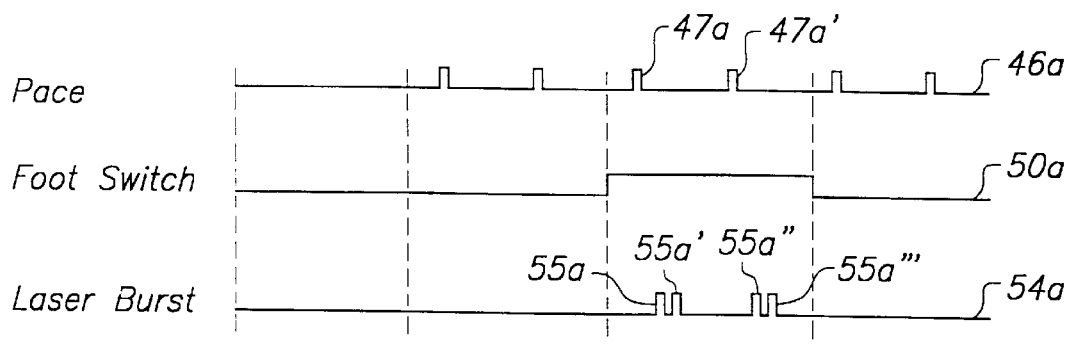
FIG. 3a is a timing diagram for revascularization with heart pacing including a foot switch signal.

FIG. 3a includes pace signal 46a, footswitch signal 50a, and a laser burst signal 54a. Signal 55a occurs after pace signal 46a is active at 47a. Thus, a revascularization occurs after the heart is paced. As shown, laser bursts 55a and 55a' occur only when foot switch signal 50a is active. Laser burst signals 55a and 55a' occur after pace signal 47a but before pace signal 47a'. Laser burst signals 55a " and 55a"' occur after the pace signal 47a'.

By selecting the time delay between a pace signal 47a and a revascularization event 54a, the revascularization event can be caused to occur at a selected time relative to the heartbeat. This time is selected in order to reduce the possible negative effects on the heart because of irritation from the revascularization event such as causing arrhythmias or other disturbance to the heart. In one embodiment the revascularization event occurs when the heart is electrically quiet or when the heart is more still mechanically than at other times relative to the heartbeat. Footswitch signal 50a is a signal that is provided by the footswitch controlled by the surgeon. The time delay from the pace signal 47a to the revascularization event 55a can be set at a fixed value as optimally chosen to reduce problems with the heart. Alternatively, this time delay can be variable.

Figure 3B:
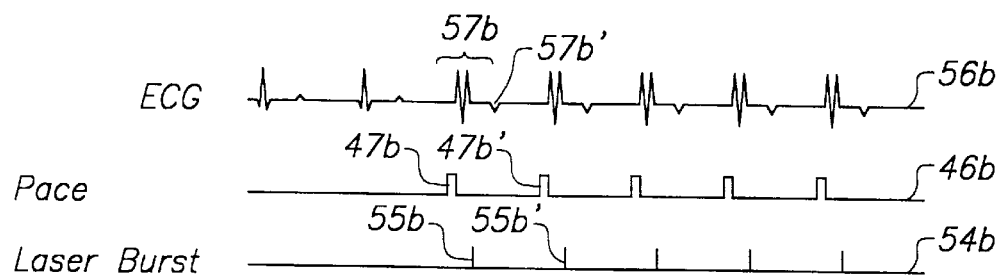
FIG. 3b is a timing diagram for revascularization with heart pacing.

As shown in FIG. 3b, the time delay between the pace signal 47b and laser burst signal 55b is set so that the laser burst signal 55b occurs after the QRS complex 57b and the T wave 57b'. The electrocardiogram signal 57b is shown for illustrative purposes and is not used to control the time at which the laser burst occurs. The heart is paced at a rate faster than the unpaced heartbeat rate. As shown on signal 56b, the time between heartbeats is greater prior to signal 47b than after signal 47b. The rate of the paced heart is faster than the rate of the unpaced heart in order to allow the pace signal 46b to control the heart. The signal from an electrocardiogram or other sensor can be used to calculate a pace rate faster than the normal unpaced heart rate and provide the pace signal 46b at this pace rate. If the heart during revascularization goes into a fast or chaotic rhythm the operator may change the rate of pacing in order to attempt to regulate the heart rate and return the heart rate to a rate closer to the normal heart rate.

Figure 3C:
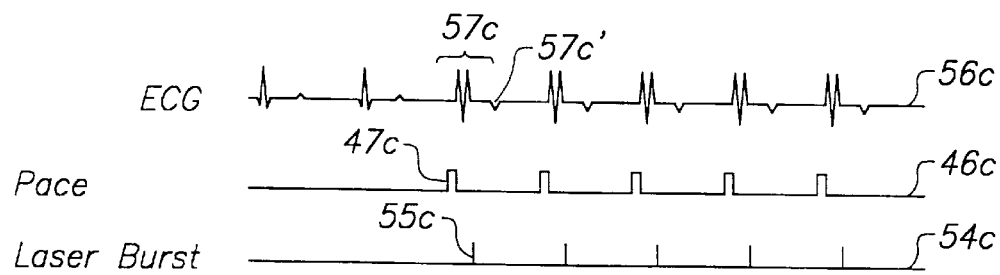
FIG. 3c is a timing diagram for revascularization with heart pacing.

FIG. 3c includes electrocardiogram signal 56c, pace signal 46c, and laser burst signal 54c. Electrocardiogram signal 56c is not used to control the laser burst. As can be seen in the FIG. 3c, the heart beats in response to pace signal 46c as seen in electrocardiogram signal 56c which indicates heartbeats. The time delay between pace signal 47c and laser burst signal 55c is such that the laser burst occurs during the heartbeat as represented by signal 57c. Alternatively, the laser burst can be timed to occur simultaneously or substantially simultaneously with the pacing signal 47c.

Figure 3D:
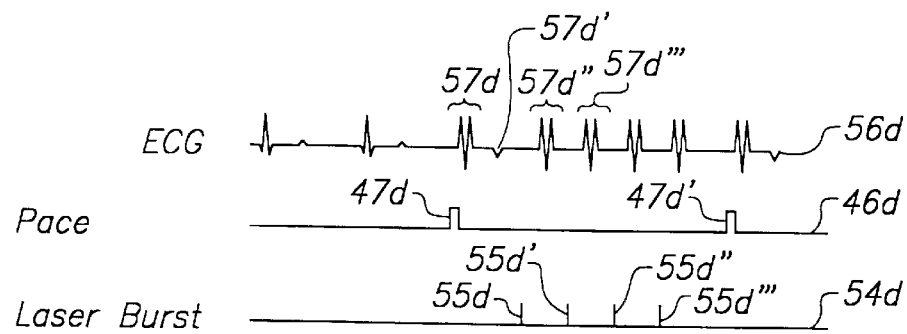
FIG. 3d is a timing diagram for revascularization with heart pacing including laser pulses that cause heartbeats.

FIG. 3d is a timing diagram for revascularization with heart pacing including laser pulses that cause heartbeats. Electrocardiogram signal 56d is not used to control the laser burst or the periods at which they occur. As seen in the FIG. 3d, the heart rate before pace signal 47d is slower than the heart rate after pace signal 47d. Between the pace signal 47d and 47d' the heart beats in response to the laser bursts 55d, 55d', 55d", and 55d"'. As shown in FIG. 3d the revascularization events or the laser bursts occur at a time at which they cause the heart to beat.

Figure 3E:
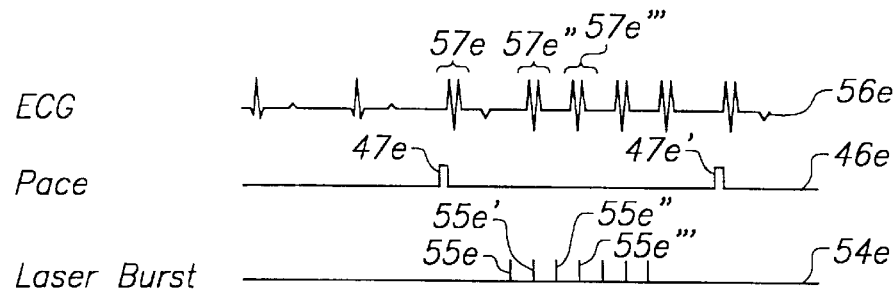
FIG. 3e is a timing diagram for revascularization with heart pacing including laser pulses that cause heartbeats and including multiple laser pulses per heartbeat.

FIG. 3e includes electrocardiogram signal 56e, pace signal 46e, and laser burst signal 54e. There are no signals from the pacer between signal 47e and 47e'. Laser 28 is used to pace the heart during this period. Further, multiple pulses of the laser occur for each heartbeat. For example, after the laser pulse 55e which causes the heart to beat as demonstrated by electrocardiogram signal 57e", a second laser pulse occurs at signal 55e', which does not cause the heart to beat in response.

Figure 3F:
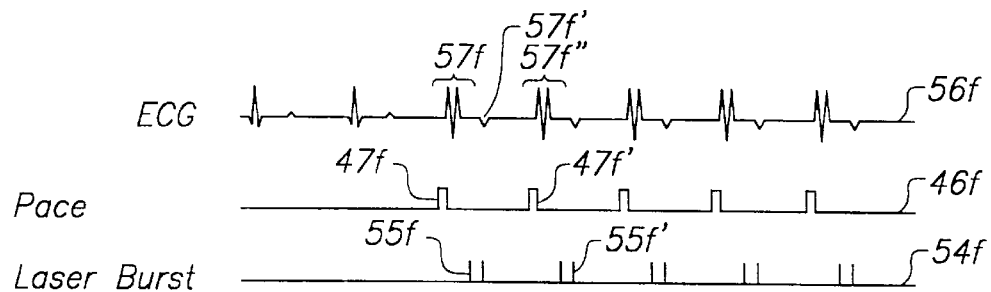
FIG. 3f is a timing diagram for revascularization with heart pacing including multiple laser pulses per heartbeat.

FIG. 3f illustrates revascularization with heart pacing including multiple laser pulses per heartbeat cycle. FIG. 3f includes electrocardiogram signal 56f, pace signal 46f, and laser burst signal 54f. Electrocardiogram signal 56f or signal from another type of sensor (e.g. pressure sensor) can be used to observe whether the heart is beating efficiently and to disable the laser if the heart is not beating. Laser bursts 55f and 55f' occur after pace signal 47f and after R wave 57f and before T wave 57f'. Multiple laser bursts 55f and 55f' are provided in order to allow for possibly greater depth of revascularization per heartbeat cycle or to create stimulation zones with or without connecting channels. The rate at which the heart is paced is faster than the unpaced rate of the heart. As seen in FIG. 3f, the time between heartbeat signals on the electrocardiogram signal 56f is greater before first pace signal 47f than the time between heartbeat signals after pace signal 47f. It may be desirable to cause a revascularization event to occur after a depolarization of the heart and before a repolarization of the heart.

Figure 3G:
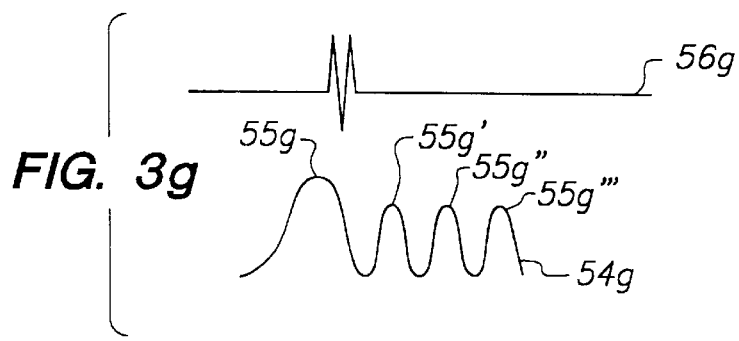
FIG. 3g is a timing diagram for revascularization with heart pacing including multiple laser pulses of different intensities.

As shown in FIG. 3g, first pulse 55g is stronger than subsequent pulses 55g, 55g', 55g", and 55g"' in order to allow the first pulse to pace the heart and subsequent pulses to be used to revascularize or create a channel into the heart. The heart beats in response to first laser pulse 55g. Alternatively, first laser pulse 55g can be smaller than the subsequent ones so that the first pulse is large enough to pace and subsequent ones are larger for greater revascularization.

The apparatus and method described above may be used in a percutaneous procedure, in a minimally evasive surgery (MIS) procedure, or other surgical procedure. In a percutaneous procedure, a catheter is introduced into the vasculature and revascularization events are created using the catheter. In a MIS procedure, apparatus to perform revascularization is introduced into the body through a port, an opening that is small relative to the opening used in typical heart surgery. Other surgical methods can be used with paced revascularization described.

Figure 4A:
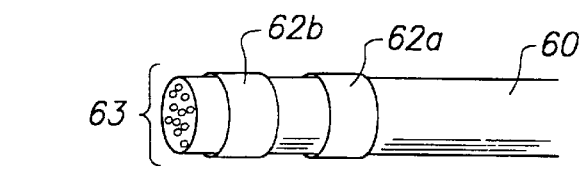
FIG. 4a is a perspective view of a fiber optic catheter with pacing leads.

As illustrated in FIG. 4a electrode 62a and electrode 62b are mounted on catheter 60 near the distal end of catheter 60. Fiber optic fibers 63 are located in the interior of catheter 60 and extend to the distal end thereof in order to provide laser energy to the heart for creating channels and revascularization. Electrodes 62a and 62b provide artificial energy that causes a created heartbeat in the heart. This artificial energy is a pacing signal. Electrodes 62a and 62b are located near the distal end of catheter 60 in order to provide a pacing signal close to the location of revascularization. Catheter 60 can be used for ventricular pacing and artrial pacing by placing the electrodes 62a and 62b on a location and on catheter 60 so that they are in either the atrium or ventricle as chosen. Electrodes 62a and 62b can be used to pace directly into those locations of the heart. A sensor such as a pressure transducer can also be coupled to the catheter 60 along with the pacing electrodes 62a and 62b.

Figure 4B:
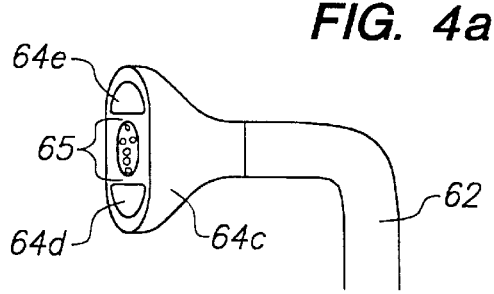
FIG. 4b is a perspective view of a fiber optic laser energy delivery device handpiece with pacing leads.

FIG. 4b is a perspective view of a fiber optic laser energy delivery device handpiece 62 with pacing leads as could be used for surgical paced revascularization or, with modifications, in MIS applications. Handpiece 62 is for controllably advancing a fiber. Such a handpiece is available under the name Sologrip i' from Eclipse Surgical Technologies, Sunnyvale, Calif. FIG. 4b shows electrode end 64c, electrode 64e, electrode 64d, and fiber optic fibers 65. The electrode 64d and electrode 64e are located at the distal end of the laser energy delivery device handpiece 62 and extend though the laser energy delivery device handpiece 62. The location of the electrodes 64d and 64e provides the pacing signal close to the location of revascularization.

FIG. 4c shows a perspective view of a piercer 66 with an electrode 68. Electrode 68 is located at the distal end of piercer 66, and insulator 70 is located around the distal end of the piercer 66. The piercer can be used for revascularization. Piercer 66 may be a hollow needle, thereby allowing the laser fiber optic device to extend therethrough. Alternatively, piercer 66 may be angled fibers. Piercing, particularly when performing TMR from the epicardial surface is helpful to reduce acute bleeding, to anchor the device to the beating heart, and to reduce adhesions between the epicardium and the pericardium.

FIG. 4d is a cross sectional view of an electrically controllable mechanical cutter. The mechanical cutter includes a piercer 72, a spring 74, and a solenoid 76. Piercer 72 is driven by spring 74 as controlled electrically by solenoid 76. This construction allows this mechanical piercer 72 to be electronically controlled. The time of the piercing can be set relative to the pace signal of the heart. Alternatively, the piercing can be timed so as to cause the heart to beat.

Referring now to FIGS. 5a to 5d, embodiments of a catheter with fiber optics 86 are illustrated. The FIGS. 5a to 5d show fiber bundles; however, it is appreciated that single fibers, waveguides, lenses used with fibers, or lenses in articulated arms could also be used. In FIG. 5a the fibers 86 are surrounded by handle 80. A slot 82 is configured to receive a control knob. FIG. 5b shows a handle 80' and a slot 84 through handle 80'. Slot 84 may be used for a control knob or control block to slide fibers 86 through the body of handle 80. FIG. 5c shows glass fibers 86 in a bundle of fibers. Alternatively, a single fiber, wave guide, or $CO_2$ laser handpiece may be used. FIG. 5d shows a protective sheath 90 over a bundle of fibers including fibers 86. A marker 88 is positioned around fibers 86. Marker 88 is comprised of tantalum or similar material. Epoxy 92 holds fibers 86 together.

In each of the paced revascularization procedures (percutaneous, MIS, and other surgical procedures), any pacemaker lead placement method can be used. For example, pacemaker leads may be placed on a catheter, as described above. A pacing lead can be introduced percutaneously by introducing pacing leads into the p. saphenous vein and through the right femoral vein (medial to the right femoral artery), then threading the lead up through the inferior vena cava and into the right ventricle, and letting the lead lay on the right ventricle during the procedure. A pacing lead may be attached directly to the heart during surgery. A pacing lead can be introduced in a MIS approach wherein the pacing wire is placed directly on the epicardium through a port and is attached to the right ventricle with a small suture needle during the procedure. As indicated above, as with the other approaches to introducing pacing leads, the MIS approach of pacing lead placement can also be used with any of the paced revascularization procedures.

Figure 6:
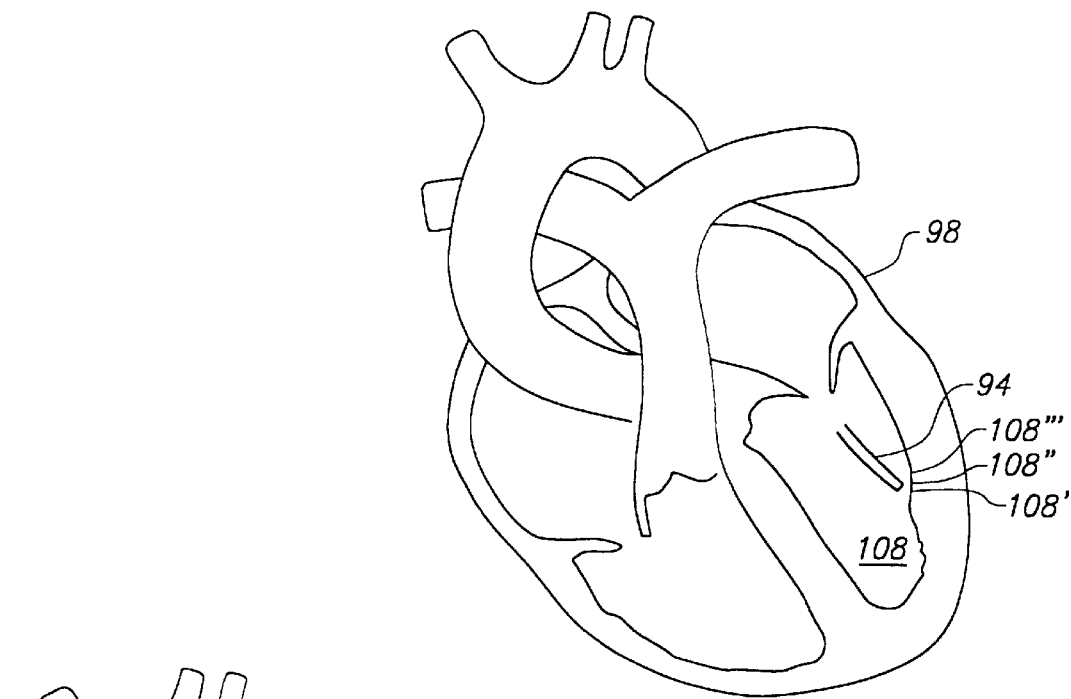
FIG. 6 is a cross sectional view of a heart with revascularization channels created in a percutaneous procedure.

As shown in FIG. 6, paced revascularization can be performed percutaneously. A revascularization device 94 is introduced percutaneously into the vasculature and moved into the heart 98. Revascularization device 94 is used to create channels 108', 108", and 108''' in heart 98. Here the channels are shown in the left ventricle 108. The revascularization channels 108', 108", and 108''' help to improve blood flow to the heart and help to stimulate the regrowth of capillaries. Channels extend from the ventricle partway through the myocardium.

Figure 7:
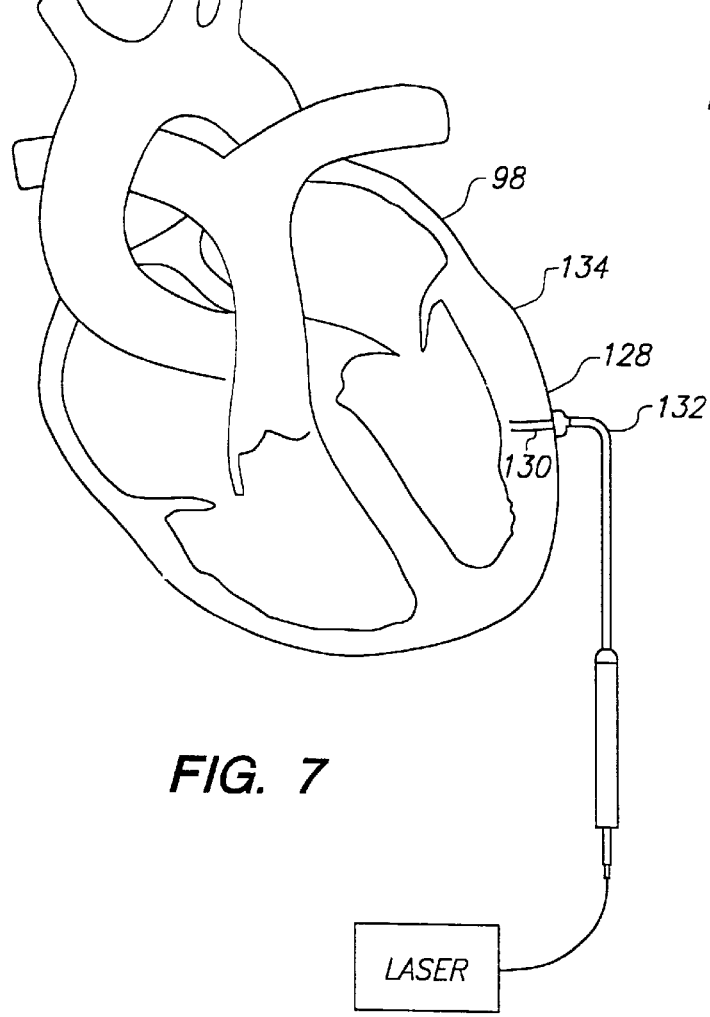
FIG. 7 is a cross sectional view of a heart with a revascularization channel created in a surgical procedure.

FIG. 7 shows surgical paced revascularization. Laser energy delivery device 132 is introduced surgically into the body and creates channel 130 through the epicardium 128. Minimally invasive surgery (MIS) can also be used for paced revascularization and can be used to create a channel 130 in the epicardium 128. Pacing leads may be placed approximately at point 134 on heart 98. Alternatively, any other method of pacing lead placement can be used, such as placing leads in the ventricle of the heart or on the laser energy delivery device 132.

Figure 8A:
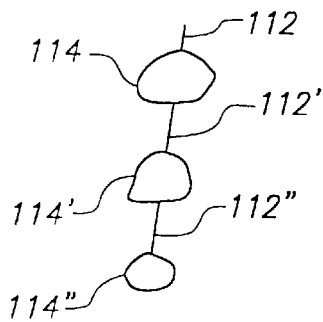
FIG. 8a is a view of channels and pockets created in heart tissue.
Figure 8B:
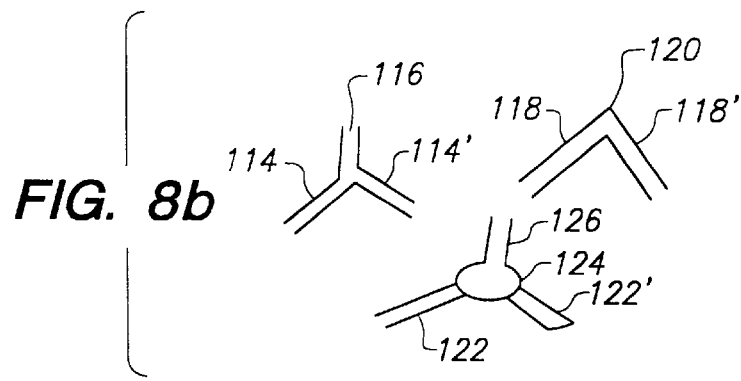
FIG. 8b is a view of multiple legs created from channels in heart tissue.

As shown in FIG. 8a, narrow stimulation zones created as narrow channels 112, 112', and 112" can be produced in heart tissue. Narrow channels 112, 112', and 112" can be created between created pockets 114, 114', and 114" in heart tissue. Narrow channels may close and pockets may remain open. As shown in FIG. 8b, channels may also have multiple legs 114 and 114' extending from a single entry 116. FIG. 8b also shows legs 118 and 118' extending from entry 120. Multiple legs 122 and 122' may extend from a pocket 124, which is created from a single entry 126. Some of the legs may not extend through the myocardium. Such legs that do not extend through the myocardium can be referred to as blind channels and can be used for depositing drugs directly into heart tissue.

Figure 9:
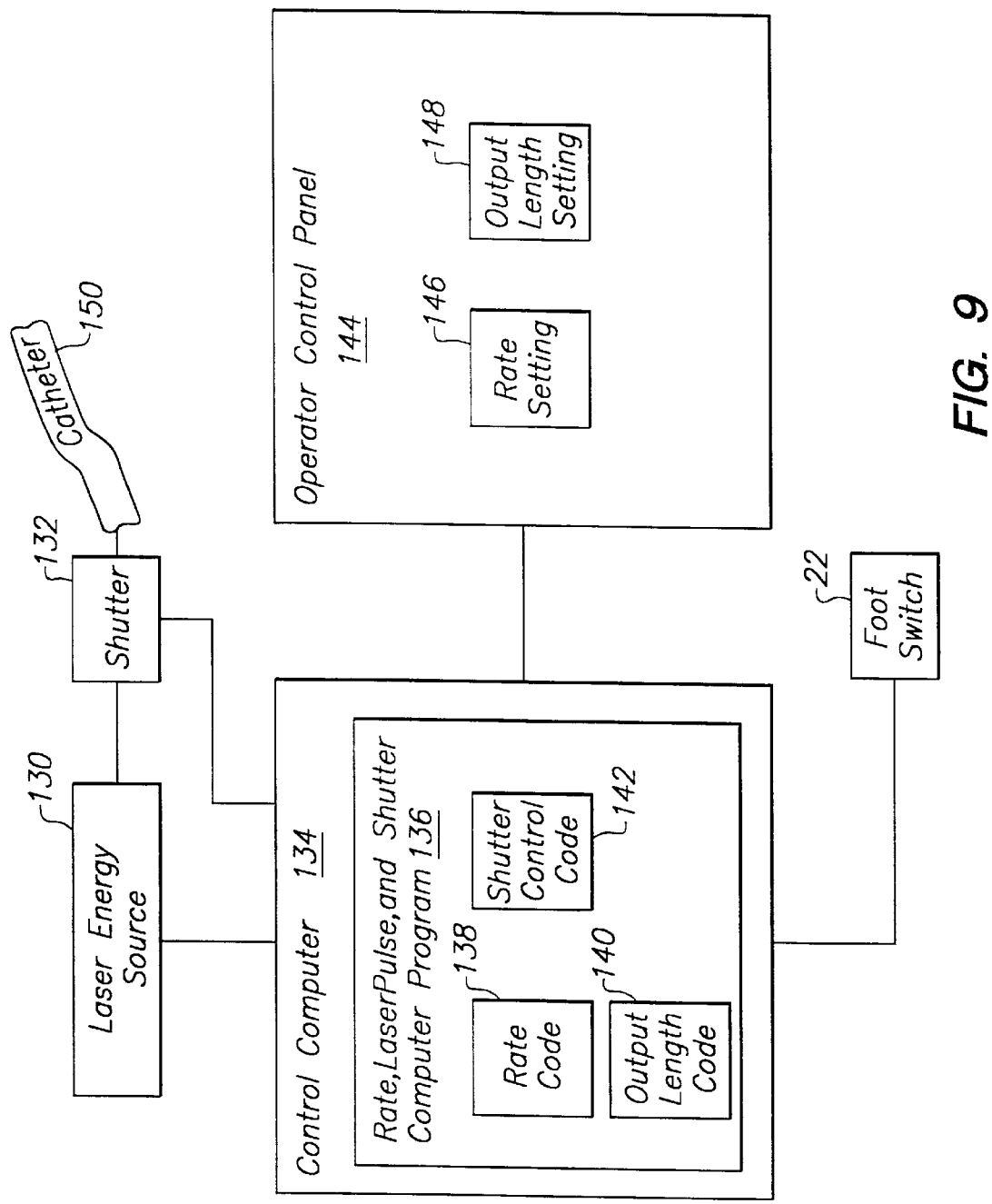
FIG. 9 shows a system with a computer program for laser revascularization.

FIG. 9 shows a system with a computer program for a laser revascularization. In FIG. 9 laser energy source 130 is coupled to shutter 132, which shutters energy to ensure that the laser energy is within preset limits before laser energy is delivered through catheter 150. Control computer 134 is coupled to laser energy source 130 for controlling the rate of firing of laser energy source. Control computer 134 is coupled to shutter 132 for controlling the rate and timing of shutter.

Operator control panel 144 includes a rate setting 146 and an output length setting 148. An operator can input a rate via a rate setting 146 to control the number of outputs per time period. The operator can input the length of an output via the output length setting 148. Operator control panel 144 is coupled to control computer 134 and provides burst rate and output length to control computer 134 as selected by the operator.

Control computer 134 includes rate, output length, and shutter computer program 136. Rate, output length, and shutter computer program 136 controls the rate, output length, and shutter setting for laser energy source 130 and shutter 132. Rate, output length, and shutter computer program 136 includes rate code 138, output length code 140, and shutter control code 142. Rate code 138 controls the number of outputs per time period. Output length code 140 controls the length of an output. Shutter control code 142 causes shutter 132 to block laser energy from laser energy source 130 in order to ensure that laser energy from laser source 130 is within preset limits. Control computer may be implemented as a personal computer running a program recorded on a computer readable medium such as a floppy disk, a hard disk, a ROM, an EPROM, an application specific integrated circuit (ASIC), a RAM, a compact disc, or any other medium or circuit capable of storage logic or instructions. Foot switch 22 is coupled to control computer 134 and allows operator to activate laser energy source 130 under control of control computer 134.

Figure 10:
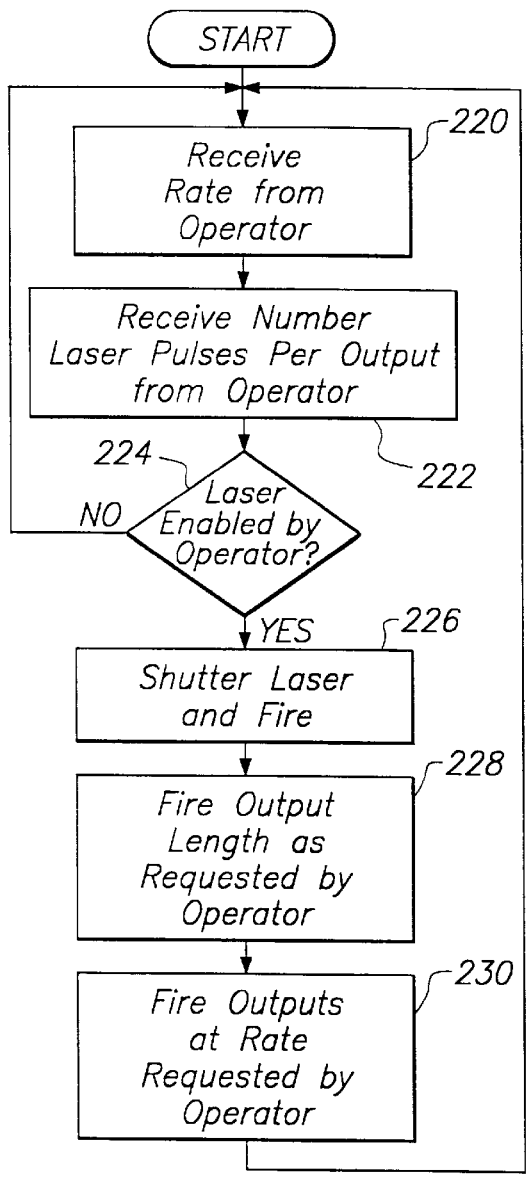
FIG. 10 is a flow chart showing a program for revascularization with laser revascularization.

FIG. 10 is a flow chart showing a program for revascularization with multi pulse revascularization. A rate is received from the operator (block 220). Next, output length is received from the operator (block 222). If laser has not been enabled by the operator (block 224), then program returns to block 220. If laser has been enabled by operator (block 224), program shutters laser and fires (block 226). Laser is shuttered in order to allow laser to ensure laser source 130 is within preset limits. Next, laser is fired for an output length as requested by the operator (block 228). Laser continues to fire outputs comprising sets of pulses at a rate requested by the operator (block 230). The program continues to cycle and returns to block 224 and laser continues to produce outputs as long as laser is enabled by operator.

Figure 11:
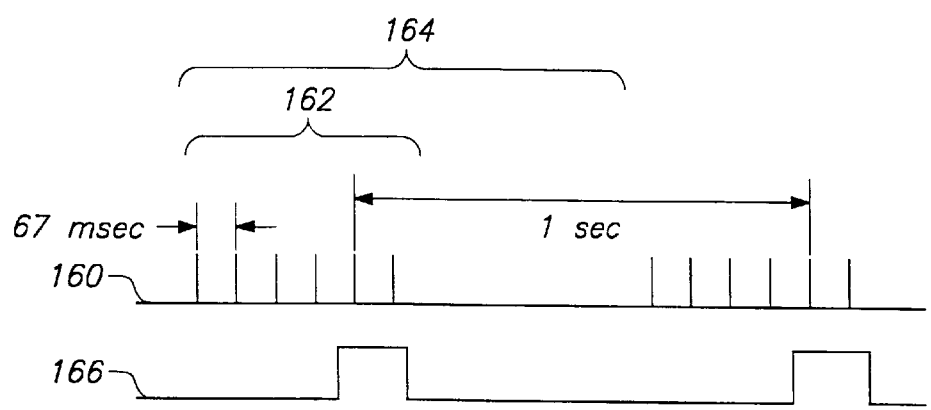
FIG. 11 is a timing diagram showing laser outputs.

FIG. 11 is a timing diagram showing laser outputs. FIG. 11 shows at least one heart beat cycle 164. In FIG. 11, heart beat cycle 164 is one second long. FIG. 11 also shows at least one laser output 162 on trace 160. Laser output 162 comprises a set of pulses delivered over a period of time that is generally not longer than the heart beat cycle 164. Shutter trace 166 shows the action of shutter to allow only the last two laser pulses within laser output to pass to the catheter and cause a revascularization in the heart. Laser output 162 includes laser pulses that are spaced by 67 milliseconds. Alternatively, laser output may comprise a continuous wave of laser energy in the shape of a smooth wave or other shaped wave. Two laser pulses may be delivered per output, or, alternatively, a set of pulses in the range of 1 to 4 may be delivered per output.

Laser output 162 is shorter than the period of time from Q wave to a T wave of a heart before revascularization. A rest period is provided between laser outputs. The rest period is slightly shorter than the time period from a T wave to a Q wave of the heart before revascularization.

FIG. 12a–12d are timing diagrams showing laser outputs and heart waves in an experiment with a canine subject. ECG signals are represented by the traces 170, 180, 200, and 210. An R-wave detect signal is shown as traces 172, 182, 202, and 212. In these figures the R-wave detect was not connected to the subject. A pacemaker signal is shown on traces 174, 184, 204, and 214. In this data, the pacemaker was not connected to the subject. Laser outputs are shown in traces 176, 186, 206, and 216. Laser shutter is shown in traces 178, 188, 208, and 218.

Laser output is performed using a laser such as a $CO_2$ laser, an excimer laser, or a holmium laser. Other lasers may also be used. The holmium laser is a solid state laser requiring some settle down time. In order to allow the holmium laser to settle down three or four laser pulses of the holmium laser are fired but are not delivered to the patient. These pulses are shuttered from the catheter 150 using the shutter 132 as controlled by shutter control code 142. Not all lasers require the settle down time and thus not all lasers require a shutter.

In one embodiment, the heart rate is determined, and the time between outputs is set to be about five outputs faster per minute than the heart beat rate that is determined before revascularization. Two laser pulses may be delivered to the patient per laser output. It is desirable to deliver somewhere in the range of one to five laser pulses per laser output. The number of laser pulses delivered per laser output may be limited by the number of laser pulses that may cause the heart to beat again prior to repolarization. The rate of laser outputs may be limited by the maximum acceptable heart rate for the patient as corrected for the patient's age. Also, the length of the output should not greatly infringe upon the rest time between laser outputs. The number of pulses per output is variable and selectable depending upon laser parameters, desired tissue effect, and preventing the heart from beating faster than its optimally acceptable rate. In another embodiment, the rate of laser outputs per time period is set to ten outputs faster per minute than the heart beat rate that is determined before revascularization. In yet another embodiment, the rate of laser outputs per time period is set to twenty outputs faster per minute than the heart beat rate that is determined before revascularization. In another embodiment the rate of pacing by a pacemaker or by laser outputs may be slightly slower than the heartbeat rate before revascularization.

Prior to revascularization, the pacemaker can be used to synchronize the heartbeat with the pattern that laser outputs will have. Between one and three laser pulses may be used before revascularization to synchronize the heartbeat. During laser revascularization, the pacemaker can be shut off as laser outputs are delivered to the patient. Thus the laser can be used to pace the heart. Upon completion of delivery of laser outputs, the pacemaker may again resume pacing the heart to restore normal rhythm. Between one and three pacemaker pulses can be used to pace the heart after completion of laser revascularization. As revascularization is performed, the operator maintains a steady but low level of push force on the fiber optic, in order to avoid possible increased risk of unsustained or sustained arrhythmia's from excessive force on the fiber optic.

A laser output can include a spacing of laser pulses or continuous laser energy output within a single laser output to cause potentially only one heart beat in response. The laser energy can be delivered to approximately simulate the normal rhythm of the heart. A selectable number of pulses is provided with the pulses close together in an output and the interval between each pulse within an output is short enough such that the total time per output is short relative to a single heart cycle. The time between outputs is also variable and selected based upon a patient's heart rate. The variable time between outputs generally is set to provide the next output at a time which is slightly faster than the patient's resting heart rate, for example at a time which is approximately five beats per minute faster than the patient's resting heart rate, before revascularization. A laser energy output pattern set close to a normal heart rhythm pattern may result in capture of the heart rate by the laser thereby allowing the laser to pace the heart. Such a capture may not necessarily occur, in which case an ECG tracing may illustrate two heart beats, not one during a cycle in which normally one heart beat would occur. Such a pair of heartbeats is a "couplet." Alternatively, although only one heartbeat per cycle may be visible, two superimposed heartbeats may be occurring. Although operating the laser so as to stimulate heartbeats does not require use of a pacemaker, a pacemaker may be used to initiate the process. When operated with a pacemaker, the pacemaker creates the first beat prior to delivery of an output. The sequence is pace, laser output. Use of a pacemaker may prevent the situation where a pair of heartbeats occurs in each cycle.

Figure 13:
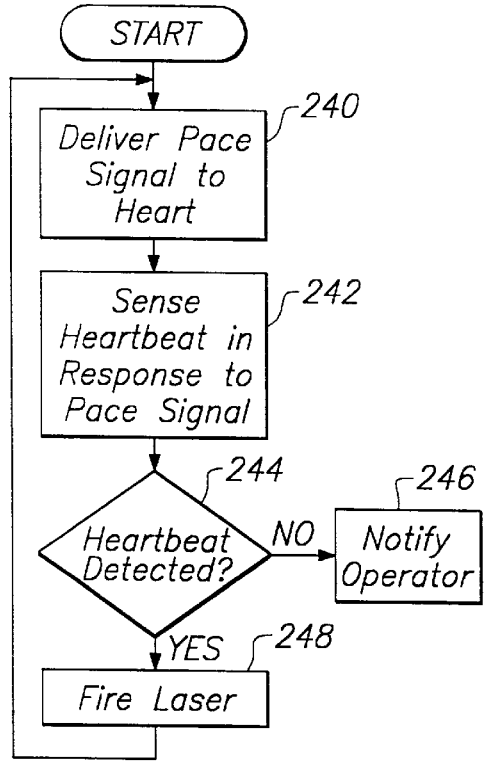
FIG. 13 is a flow chart showing a program for revascularization with sensor verify.
Figure 12A:
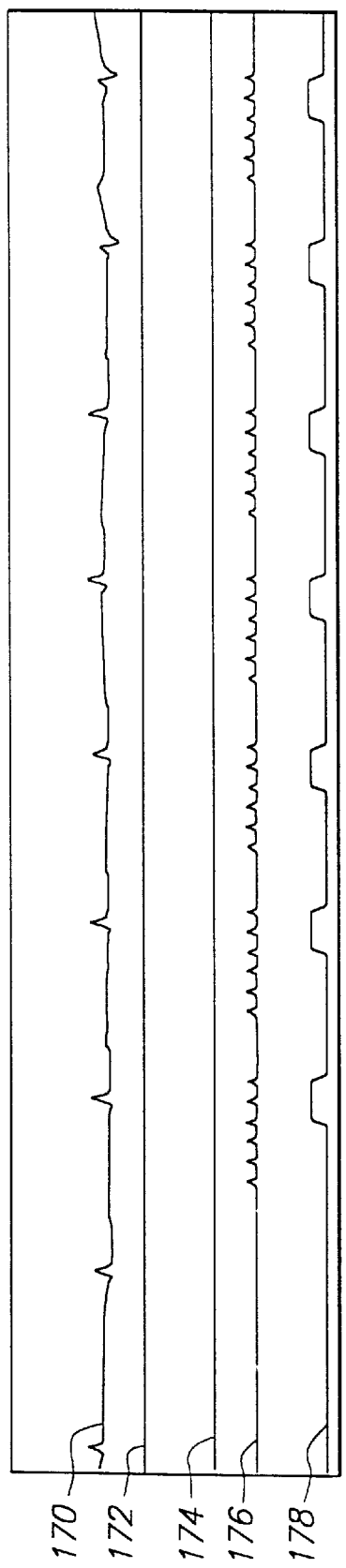
FIGS. 12a–12d are timing diagrams showing laser outputs and heart waves.
Figure 12B:
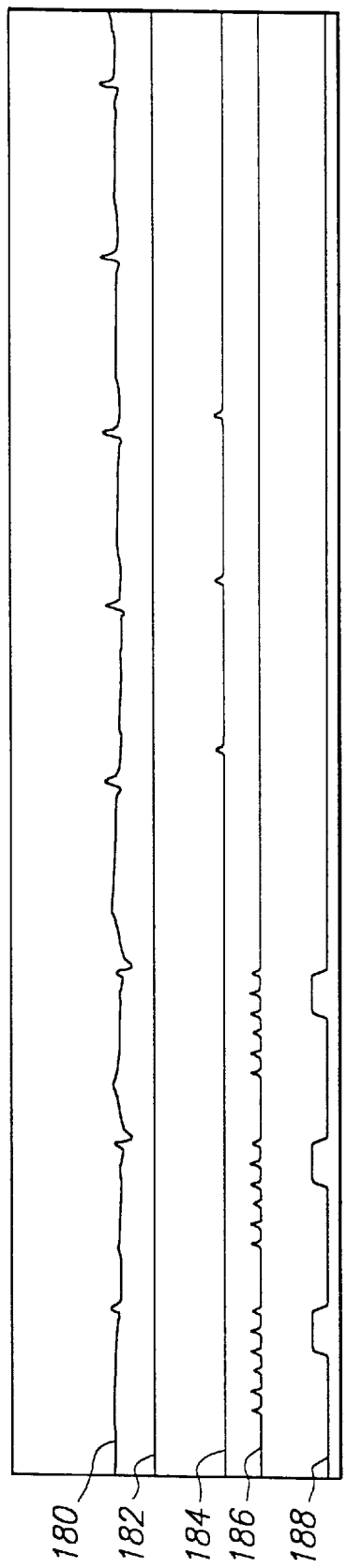
Figure 12C:
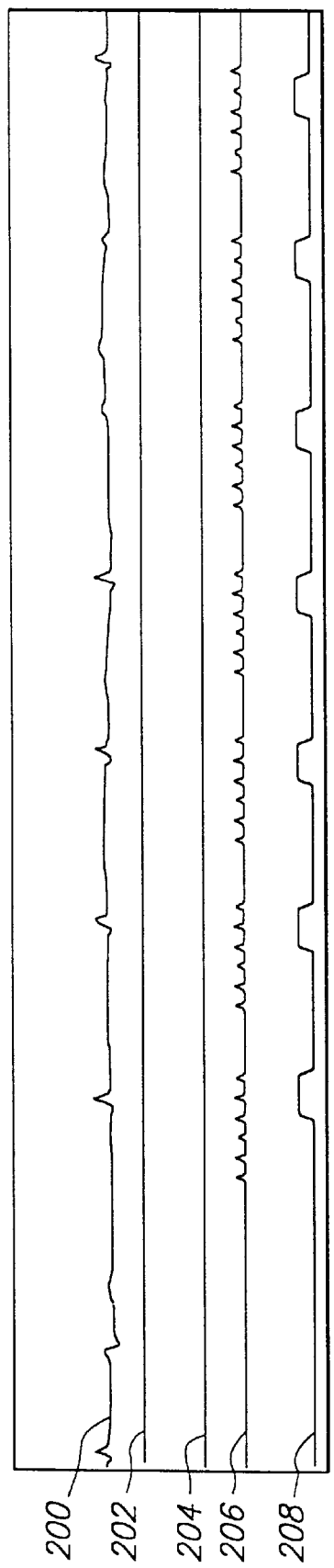
Figure 12D:
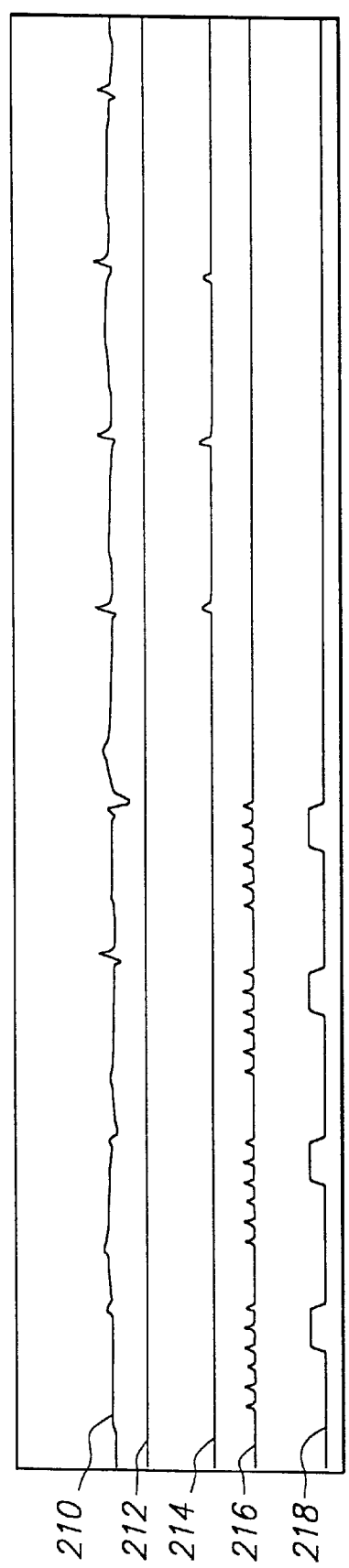

FIG. 13 is a flow chart showing a program for revascularization with sensor verify. The program shown in FIG. 13 may be operated on a computer, implemented in electronics, or may be automated in any other way, or may be performed by a human operator. If performed by a computer, the program may be implemented on a personal computer, a microprocessor, or any other computer, and the program may be stored on any computer readable medium or logic.

A pace signal is delivered to the heart (block 240). The heart beat is sensed to determined whether the heart has beat in response to the pace signal (block 242). If a heart beat is not detected (block 244), then the operator is notified (block 246). If a heart is detected (block 244), the laser is fired (block 248). Next, the program continues to block 240. The program senses whether the heart beat has responded to the pace signal in order to avoid delivering a revascularization event if the heart has not beat in response to a pace signal.

FIG. 14 is a flow chart showing a program for revascularization with sensor verify and pace rate calculation. The patient's age is received from the operator (block 260). The patient's heart rate is measured before revascularization (block 262). A pace rate is calculated based on age of the patient and the heart rate before revascularization (block 264).

The program waits a period as determined by the pace rate. The period is the inverse of the pace rate subtracting for time used during the subsequent steps of the program (block 266). If the footswitch is enabled (block 268), the laser is fired (block 272). If the footswitch is not enabled (block 268), a pace signal is delivered to the heart (block 270). After the laser is fired in block 272, the program proceeds to block 274. After delivering a pace signal to the heart in block 270, the program proceeds to block 274. If a heart beat is not detected (block 274), the operator is notified (block 276). Otherwise, the program returns to block 266 to wait for the period determined by the pace rate.

The heart beat may be detected using any type of sensor including but not limited to an ECG, a pressure sensor, a flow measurement device, or an ultrasound device. An ultrasonic device can monitor, for example, thickness of the myocardium and determine whether a change has occurred. The change in thickness can be correlated with the heart beat. Thus, an ultrasonic device can be used to determine whether the heart has beat in response to a pace signal and that information can be used to temporarily shut off the revascularization device if the heart does not beat in response to a pace signal.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claim and their equivalents.

What is claimed is:

1. An apparatus for treating a patient's heart, the apparatus comprising:

a catheter;

a laser energy source coupled to the catheter;

a shutter positioned to block energy from the laser energy source when the shutter is closed; and a control circuit that is configured to close the shutter to block laser energy and to open the shutter to allow the laser energy source to deliver an output of energy to the patient's heart, wherein the control circuit is configured to deliver the output of laser energy over a first time period that is sufficiently short so that the output causes no more than one heartbeat, and the laser energy source and catheter are adapted to cause heartbeats by the delivery of the laser energy.

2. The apparatus of claim 1, wherein the control circuit is configured to deliver the output of laser energy wherein the first time period is shorter than a second time period from a Q wave to a T wave of the heart.

3. The apparatus of claim 1, wherein the control circuit is configured to deliver a second output of laser energy after a second time period equal to or shorter than a third time period from a T wave to a Q wave of the heart.

4. The apparatus of claim 1, wherein the control circuit is configured to deliver outputs of laser energy at a rate equal to or faster than the patient's heart rate before revascularization.

5. The apparatus of claim 4, wherein the rate of outputs is 20 outputs per minute faster than the patient's heart rate before revascularization.

6. The apparatus of claim 1, wherein the control circuit is configured to deliver the output of laser energy wherein the output of laser energy comprises a set of pulses of laser energy.

7. The apparatus of claim 6, wherein the set of pulses comprises a number of laser pulses in the range 1 to 4.

8. The apparatus of claim 6, wherein the control circuit is configured to deliver laser pulses in the set of laser pulses at a rate greater than 15 laser pulses per second.

9. An apparatus for treating a patient's heart, the apparatus comprising:

a catheter, a pacemaker;

a laser energy source coupled to the catheter for delivering laser energy to the patient's heart;

a shutter configured to block laser energy from the laser energy source; and a control circuit coupled to the pacemaker which is configured to cause the pacemaker to cause only one heartbeat per the output of laser energy and to control opening and closing of the shutter.

10. The apparatus of claim 9, wherein the control circuit is configured to deliver a pace signal to the heart before causing the laser energy source to deliver the output of laser energy.

11. The apparatus of claim 9, wherein the laser energy source comprises a $CO_2$ laser.

12. The apparatus of claim 7, wherein the control circuit is configured to deliver between two and four pace signals to the heart before causing the laser energy source to deliver the output of laser energy.

13. The apparatus of claim 9, wherein the control circuit is configured to deliver a pace signal to the heart after causing the laser energy source to deliver the output of laser energy.

14. The apparatus of claim 3, wherein the control circuit is configured to deliver between two and four pace signals to the heart after causing the laser energy source to deliver the output of laser energy.

15. The apparatus of claim 13, wherein the control circuit is configured to deliver the output of laser energy over a first time period that is shorter than a second time period from a Q wave to a T wave of the heart and wherein the control circuit is configured to deliver a second output of laser energy after a third time period shorter than a fourth time period from a T wave to a Q wave of the heart.

16. The apparatus of claim 9, wherein the laser energy source comprises a medical laser having a wavelength in the range of 308 nanometers to 10.6 micrometers.

17. The apparatus of claim 9, wherein the laser energy source comprises a holmium laser.

18. The apparatus of claim 10, wherein the control circuit is configured to deliver the output of laser energy the first time period that is shorter than a second time period from a Q wave to a T wave of the heart and wherein the control circuit is configured to deliver a second output of laser energy after a third time period shorter than a fourth time period from a T wave to a Q wave of the heart.

19. The apparatus of claim 9, wherein the laser energy source comprises an excimer laser.

20. A method of treating a heart, the method comprising:

providing a laser energy source;

introducing a laser energy delivery device coupled to the laser energy source to the heart;

using the laser energy delivery device to deliver energy source to the heart cause a revascularization event in the heart; and causing the laser energy delivery device to deliver from the laser energy source an output of laser energy sufficient to cause only one heartbeat per the output of laser energy.

21. The method of claim 20 comprising:

delivering the output of laser energy for a first time period shorter than a second time period from a Q wave to a T wave of the heart.

22. The method of claim 20 comprising:

delivering a second output of laser energy after a second time period shorter than a third time period from a T wave to a Q wave of the heart.

23. The method of claim 20 comprising:

repeatedly delivering outputs of laser energy at a rate faster than the patient's heart rate before revascularization.

24. The method of claim 23, wherein the rate is faster than the patient's heart rate before revascularization by fewer than 20 outputs per minute.

25. The method of claim 20, wherein the output of laser energy comprises a set of pulses of laser energy.

26. The method of claim 20, comprising:

introducing a catheter coupled to the laser energy source into the heart in a minimally invasive surgery (MIS) procedure.

27. The method of claim 20 comprising:

pacing the heart before delivering the output.

28. The method of claim 20 comprising:

pacing the heart after repeatedly delivering outputs of laser energy.

29. An apparatus for treating a patient's heart, the apparatus comprising:

a catheter;

a laser energy source coupled to the catheter;

a shutter positioned to block energy from the laser energy source when the shutter is closed; and a control circuit that is configured to close the shutter to block laser energy and to open the shutter to allow the laser energy source to deliver an output of energy to the patient's heart, wherein the control circuit is configured to deliver the output of laser energy over a first time period wherein the output of laser energy is sufficient to cause one heartbeat, and the laser energy source and catheter are adapted to cause heartbeats by the delivery of the laser energy.

30. The apparatus of claim 29, wherein the control circuit is configured to deliver the output of laser energy wherein the first time period is shorter than a second time period from a Q wave to a T wave of the heart.

31. The apparatus of claim 29, wherein the control circuit is configured to deliver a second output of laser energy after a second time period equal to or shorter than a third time period from a T wave to a Q wave of the heart.

32. The apparatus of claim 29, wherein the control circuit is configured to deliver outputs of laser energy at a rate equal to or faster than the patient's heart rate before revascularization.

33. The apparatus of claim 32, wherein the rate of outputs is 20 outputs per minute faster than the patient's heart rate before revascularization.

34. The apparatus of claim 29, wherein the control circuit is configured to deliver the output of laser energy wherein the output of laser energy comprises a set of pulses of laser energy.

35. The apparatus of claim 34, wherein the set of pulses comprises a number of laser pulses in the range 1 to 4.

* * * * *